United States Patent [19]

Pelley et al.

[11] 4,158,049

[45] Jun. 12, 1979

[54] **ANTIGEN FRACTION OF *SCHISTOSOMA MANSONI* EGGS SUITABLE FOR TESTING FOR SCHISTOSOMIASIS**

[75] Inventors: Ronald P. Pelley, Cleveland; Kenneth S. Warren, Cleveland Heights, both of Ohio

[73] Assignee: Edna McConnell Clark Foundation, New York, N.Y.

[21] Appl. No.: 727,205

[22] Filed: Sep. 27, 1976

[51] Int. Cl.$^2$ .................. G01N 33/16; A61K 39/00; A61K 43/00

[52] U.S. Cl. .................................... 424/1; 424/9; 424/88

[58] Field of Search .................. 424/1, 1.5, 9, 88; 195/103.5

[56] References Cited

U.S. PATENT DOCUMENTS 3,860,483   1/1975   Senft ........................................ 424/9

OTHER PUBLICATIONS

Boros et al., Journal of Experimental Medicine, vol. 132, No. 3, Sep. 1, 1970, pp. 488-507.

Colley, The Journal of Immunology, vol. 115, No. 1, Jul., 1975, pp. 150-156.

Boros, et al., The Journal of Immunology, vol. 114, No. 5, May 1975, pp. 1437-1441.

Pelley, et al., Infection and Immunity, vol. 13, No. 4, Apr. 1976, pp. 1176-1183.

*Primary Examiner*—Benjamin R. Padgett
*Assistant Examiner*—Christine M. Nucker
*Attorney, Agent, or Firm*—Sprung, Felfe, Horn, Lynch & Kramer

[57] ABSTRACT

*Schistosoma mansoni* eggs are ground to liberate soluble egg antigens which are fractionated and purified by absorption, gel filtration and/or ion exchange chromatography, and then radioactively labelled with $^{125}$I. A fraction, identified as MSA$_1$, is specific to the mature egg stage of *Schistosoma mansoni* and thus can be used to detect the presence of antibody to mature *Schistosoma mansoni* eggs in a patient's serum even as compared with mature eggs of different Schistosoma (species specific) or of *Schistosoma mansoni* worms but not mature eggs (stage specific).

12 Claims, 2 Drawing Figures

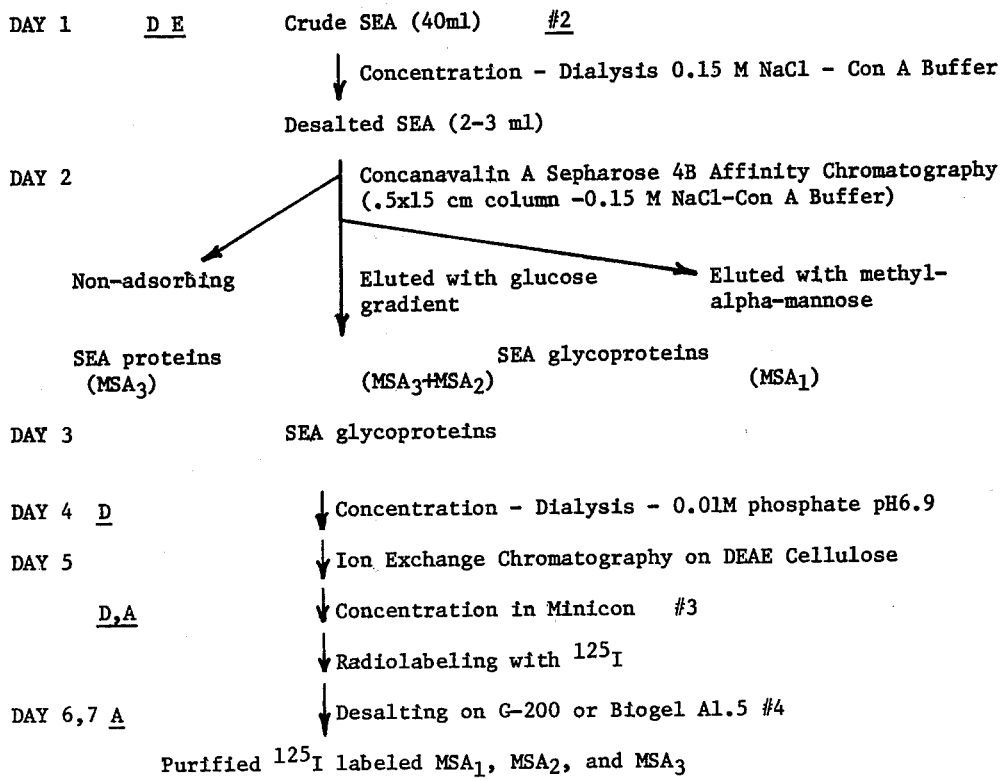

FIG. 2

NEW PROTOCOL FOR ANTIGEN PURIFICATION

DAY ONE $2 \times 10^6$ S. mansoni eggs  (50 mice)
↓ grinding in small Ten Broeck grinder in 5 ml
↓ 0.5 M NaCl - Con A Buffer
↓ Ultracentrifugation - 2 hours CRUDE SEA (5 ml)

↓ Desalting on Sephadex G-25 (2x29 cm column, 0.5 M NaCl - Con A Buffer)

Crude Desalted SEA (12 ml)

↓ Affinity chromatography on Con A Sepharose (1.6x21 cm column, 0.5 M NaCl - Con A Buffer)

Non-absorbing (16 ml)

Eluted with Methyl Alpha Mannose (12-16 ml)

SEA proteins ($MSA_3$)

SEA glycoproteins ($MSA_1$, $MSA_2$, and $MSA_3$)

↓ Concentration and dialysis

DAY TWO

↓ Iodination

↓ Desalting on Sephadex G-25

$^{125}$I-labeled $MSA_1$, $MSA_2$ with small $MSA_3$ contamination

↓ Ion exchange chromatography on DEAE cellulose

Purified, $^{125}$I-labeled $MSA_1$

ANTIGEN FRACTION OF *SCHISTOSOMA MANSONI* EGGS SUITABLE FOR TESTING FOR SCHISTOSOMIASIS

The present invention relates to the recovery of one or more antigen fractions from schistosome eggs which fractions can be used for detection of antibodies to schistosome mature eggs in the sera of patients and can thus be used as a technique for identifying infected patients.

Millions of people throughout the world suffer from schistosomiasis infections. The active material niridazole is used to treat the infection but its use is not without some risk and requires much medical attention. Thus it is desired to limit the treatment only to individuals who are reasonably certain to be so infected.

To this end various tests have been devised, some of which are capable of being applied to large populations in the field for a quick, inexpensive but approximate screening. Other tests are relatively costly but of limited accuracy. It is therefore an object of the invention to provide a specific, accurate and inexpensive test for schistosomiasis infections.

This object is realized in accordance with the present invention by utilizing a radioimmunossay technique on sera from possibly infected patients, producing a precipitate whose level of radioactivity is an index of the amount and/or nature of infection present in the patient.

BRIEF DESCRIPTION OF THE DRAWINGS

FIG. 1 shows previous protocol for antigen purification.

FIG. 2 shows antigen purification of the invention.

The radioactively labeled material used in the immunoassay is produced by a special process from schistosome egg antigens, the antigens being obtained, fractionated and purified. Starting with *Schistosoma mansoni* mature eggs the radioactively labeled fractions so obtained can detect the presence of mature eggs of schistosomes in a patient's blood, whether of *Schistosoma mansoni*, *Schistosoma japonicum* or *Schistosoma haematobium*. One of the fractions produced in accordance with the invention is even specific to the mature egg stage of *Schistosoma mansoni*, so as to be able to distinguish even between patients currently infected with *Schistosoma mansoni* and patients not infected therewith but having antibodies to *Schistosoma mansoni* by virtue of past infection therewith. The fraction can also distinguish between patients infected with *Schistosoma mansoni* and patients infected with *Schistosoma japonicum* and/or *Schistosoma haematobium*.

The procedure for obtaining the fractions involves fractionating *Schistosoma mansoni* egg antigen. Specifically, eggs are ground in water, the soluble egg antigen (SEA) entering solution which is separated from undissolved solids. The solution is subjected to affinity chromatography and elution, a third fraction hereinafter identified as $MSA_3$ (mansoni soluble antigen-third fraction) being most lightly held. A second fraction, $MSA_2$, is less lightly held and comes off on eltuion while a first fraction, $MSA_1$, is strongly held and is the last to come off. The $MSA_1$ fraction is that which is particularly desired.

Each fraction can be purified as by ion exchange chromatography and can be desalted. Each can be radioactively labeled at any stage in its recovery and the labeled fraction, particularly $MSA_1$, can be mixed in small amount with serum from a patient to form a precipitate, the amount of radioactivity in the precipitate indicating whether or not the particular patient was infected with *Schistosoma mansoni*, distinguishing between old and current infections and even between *Schistosoma mansoni* and the related *Schistosoma japonicum* and *haematobium*.

Going through the process in greater detail, the *Schistosoma mansoni* eggs can be obtained from any source but the livers or intestines of infected mice or other laboratory animals is a suitable source. The organs are chopped to release the eggs and the organs may be digested with trypsin to permit more complete extraction. The eggs are macerated in water or saline solution to liberate the soluble antigens contained therein, after which the solids are removed as by ultracentrifugation.

The supernatant liquid, containing the desired antigen mixed with other antigens, low molecular weight digestion products, salts and/or water, can be dialyzed against saline solution to remove low molecular weight material. This can be done, for example, by partially dipping a sealed tubular diaphragm containing the liquid into saline solution and applying a vacuum to the saline solution (FIG. 1). Thus through dialysis and simultaneous pervaporation the desired liquid can be freed of dialyzable material while undergoing concentration 5-fold, 10-fold or even 20- or more fold.

Alternatively, the dialyzable material can be removed by passage through a column of Sephadex ® G-25.

The concentrated solution is then subjected to affinity chromatography employing a suitable absorbent, e.g. the polygalactan sold under the tradename Sepharose ® carrying Concanavalin A bound thereto. The proportions are not at all critical but a volume of adsorbent about 3 to 4 times that of the solution has proven particularly satisfactory. The liquid which runs through the adsorbent contains a fraction, identified herein as $MSA_3$, obviously having the least affinity toward the adsorbent. Elution of the adsorbent with a dilute solution of a sugar, e.g. about 1 to 20% by weight of glucose, liberates a second fraction, $MSA_2$. Finally, a more concentrated eluant, e.g. about 1 to 2% by weight of α-methyl glucoside or α-methyl mannoside liberates a third fraction, $MSA_1$, which is the most desirable fraction in accordance with the present invention.

Each of the fractions individually can be purified to remove therefrom small portions of the other fractions. This can be effected employing gel filtration, e.g. the family of gels sold commercially as Biogel A ® or Sephadex ®, which are glucans or galactans. Each gel has holes of a certain size range to hold molecules of a particular size and, by selection of a particular gel, the desired material can preferentially be held by the gel (retarded) or not held, while the impurities are oppositely affected. If the $MSA_1$ is heavily retarded, it can be eluted as by a salt solution, e.g. about 0.9 to 4.5% by weight solution of sodium chloride.

Another preferred purification technique which can be employed either before, after or instead of the gel filtration involves ion exchange chromatography, for which diethylaminoethyl (DEAE) cellulose is a representative adsorbent. $MSA_1$ is relatively strongly held by such adsorbent whereas $MSA_3$ is lightly held and $MSA_2$ hardly held at all. Elution to remove any $MSA_3$ can be effected with dilute salt solution, e.g. about 0.02 M sodium phosphate or sodium chloride at pH 7.

Each fraction individually can be radioactively tagged at any stage or even before separation from the other fractions but desirably tagging is effected after gel filtration and/or ion exchange chromatography of the individual fractions. A suitable radioactive atom is $^{125}I$ and it can be affixed using the Chloramine T technique described in detail by Hunter in Chapter 18 of Handbook of Experimental Immunology (1967), Edited by Weir, Blackwell Scientific Publications, Oxford, England; apparently the iodine affixes itself to the phenyl ring of a tyrosine molecular unit. Other equivalent procedures may be employed. Since not all $^{125}I$ is coupled to the antigen, desalting is desirably effected before the fraction is used. For example, if iodine-labelling is done prior to gel filtration and/or ion exchange chromatography, gel filtration on Sephadex ® G-25, employing a dilute eluant, e.g. 0.01 M sodium phosphate at pH 7, will serve to hold the salts while eluting purified antigen fraction $MSA_1$. If labelling is after ion exchange chromatography, desalting on Sephadex ® G-25 or G-200 is satisfactory, employing as a buffer an about 0.14 M sodium chloride solution containing about 1 mg/cc of human serum albumin.

The purified fractions are relatively specific to the presence of Schistosoma eggs in serum, producing a precipitate. The $MSA_1$ fraction is especially sensitive, using the ammonium sulfate method to measure antigen-binding as described by Minden & Farr in Chapter 13 of Handbook of Experimental Immunology, supra, or comparable procedures. A small amount of the antigen fraction is mixed with a small amount of blood serum from a patient being tested and, after incubation, addition of salt solution, e.g. saturated sodium sulfate or, preferably, ammonium sulfate solution, produces a precipitate. The relative amount of radioactivity in the precipitate is an index of the relative amount of antibody to Schistosoma mansoni eggs in the sample. Because of the sensitivity of the test it is comparatively accurate in diagnosing the presence of the disease.

In the radioimmunoassay a small amount of rabbit serum can be added to the blood serum sample along with the $MSA_1$ and saline solution. Its purpose is to serve as a carrier and to supply mass to the precipitate which forms upon ammonium sulfate addition, i.e. the larger volume of precipitate is easier to separate and test for radioactivity level. As a rough gauge, if 50% or more of the radioactivity of the labeled $MSA_1$ ends up in the precipitate this is a positive indication. This, of course, can be shifted by using different amounts of serum, techniques, or the like.

Compared with other accepted tests, the novel technique is more reliable both positively and negatively, is relatively easy to run and requires only a small volume of serum.

Within the concepts described hereinabove, permissible variations will readily become apparent, especially once it is recognized that a fraction of such specificity is capable of isolation by some technique.

The accompanying drawing is a schematic flow sheet of the process steps involved in going from the crude Schistosoma mansoni soluble egg antigens to the purified fractions.

The invention will now be described in greater detail in the following illustrative examples wherein all parts are by weight unless otherwise expressed.

EXAMPLE 1

(a) The livers and intestines of 200 mice, which had been infected with Schistosoma mansoni in known manner, are removed, ground in enough saline solution to cover the organs, the organ solution is digested with trypsin, and the eggs filtered out and washed. The eggs are ground in saline solution and the solids are removed by centrifugation. The residual liquid comprises soluble egg antigen (SEA) and salts dissolved in water.

(b) The liquid, enclosed in a tubular dialysis membrane dipping partially into saline solution, undergoes dialysis whereby low molecular weight organic materials pass into the saline solution. At the same time a vacuum outside the membrane above the saline solution effects pervaporation of water to the extent of a 20-fold evaporation, yielding a concentrated solution which contains about 4 mg of SEA on a dry basis.

(c) The solution is subjected in known manner to affinity chromatography in a chromatographic column containing as the absorbent 10 ml of the galactan Sepharose ® carrying Concanavalin A bound thereto. After adsorption, there is recovered a fraction containing antigen which did not adhere to the adsorbent and this essentially non-adherent material is identified as $MSA_3$. Actually a small amount of the same material apparently adhered and will subsequently be separated as a part of purification.

There are then passed through the column 20 cc of a 10% by weight solution of glucose which results in recovery of an eluate fraction the principal component of which is identified as $MSA_2$.

A subsequent elution with 20 cc of a 2% solution of α-methyl glucoside (or α-methyl-mannoside) produces an eluate fraction of which the principal component is $MSA_1$ (about 1000 μg) along with small amounts of $MSA_2$ and $MSA_3$ as impurities.

(d) The $MSA_1$ eluate fraction is then labelled with $^{125}I$ using chloramine T according to the technique of Hunter, supra, the iodine atoms apparently affixing themselves to tyrosine rings. The solution is then desalted by being passed through a column 20 cm high and 0.5 cm in diameter containing Sephadex ® G-25 adsorbent, followed by elution with 50 cc of 0.01 M sodium phosphate solution at pH 7.0.

(e) The eluate is purified by ion exchange chromatography on a column containing 2 cc of diethylaminoethyl (DEAE) cellulose, followed by elution with 5 cc of 0.02 M sodium chloride (or sodium phosphate) at pH 7. Any $MSA_2$ contained in the starting material passes through the column initially and the $MSA_3$ is recovered in the elution. Further elution with 10 cc of 0.1 M sodium chloride solution produces an eluate containing 100 μg of $MSA_1$ in highly purified form, although it can be further purified slightly on a column of Sephadex ® G-200 with sodium phosphate elution as in (d).

(f) Radioimmunoassays are conducted by a modification of the method of Minden and Farr, Handbook of Experimental Immunology, Chapter 13, supra. This assay is conducted at one of two levels of sensitivity. In a screening assay to determine whether or not a patient has schistosomiasis, 5 microliters of serum is incubated with 5–10 mg of $^{125}I$ $MSA_1$ in 0.5 ml of buffer (phosphate buffered saline-10% normal rabbit serum). In a second version of this assay, which is used to quantitate levels of antibody in the serum of infected patients, 0.5 microliters of serum is incubated with antigen. After incubation at 37° C. for 15 minutes followed by a 15 minute incubation at 4° C., one half ml of cold saturated, ammonium sulfate solution is added and the mixture held at 4° C. for at least 2 hours. The precipitate containing the antibody-bound $^{125}I$ $MSA_1$ is pelleted by centrifugation at 2000 g for 15 minutes, the supernatant with the unbound $^{125}$I MSA$_1$ poured off, and radioactivity in pellet and supernatent quantitated. Percent antigen binding is given by the formula:

$$\% \text{ Antigen Binding} = \frac{CPM \text{ above background in pellet}}{CPM \text{ above background in pellet} + CPM \text{ above background in supernatant}} \times 100$$

(CPM = Counts per minute)

While Example 1 shows iodine labelling at one particular stage, it can be carried out at other stages of the purification. This is illustrated in the following example:

EXAMPLE 2

(a) The process of Example 1 is repeated through (c).

(b) The material is purified by contact with Sephadex® G-200 on which MSA$_1$ is held lightly and eluted with 0.7% sodium chloride solution.

(c) Alternatively to (b), the product of (a) is contacted with Biogel® A 1.5 which heavily retards, i.e. retains, the MSA$_1$.

(d) The product of (b) or (c) is further purified as in Example 1 (e) and iodine labelled using chloramine T as described in Example 1 (d). The $^{125}$I-labelled MSA$_1$ is then desalted on Sephadex® G-25 or G-200 using 0.14 M NaCl buffer containing 1 mg/cc of human serum albumin.

MSA$_1$, with or without $^{125}$I labelling, is a glycoprotein intermediate in size between IgG and albumin. Gel filtration analysis of purified $^{125}$I MSA$_1$ yields a molecular weight of 138,000±5,000. Its behavior (R.F. 0.33) on standard Ornstein-Davis 7.5 polyacrylamide gel electrophoresis (PAGE) is consistent with this molecular weight. These techniques partly measure the Stokes radius (largest diameter) of a molecule. Velocity sedimentation determines molecular weight by diffusion through a solution (averaged cross-sectional area). Using this technique, ultracentrifugation of $^{125}$I MSA$_1$ through sucrose gradients estimates its size at 90–100,000 daltons. The molecular weight estimated from Stokes radius is generally higher than the true molecular weight for glycoproteins that contain a substantial amount of carbohydrate. When $^{125}$I MSA$_1$ is boiled in the presence of SDS and 2-mercaptoethanol (2ME), and electrophoresed on 10% acrylamide gels containing 1% SDS (Table I, 10% SDS-2ME), it has a molecular weight of 50,000. If the velocity sedimentation estimate of the molecular weight of the intact subunit is correct, then MSA$_1$ may be a dimer composed of two isoelectrical polypeptide chains of 50,000 daltons each.

The chemical properties of MSA$_1$ are those of a classical glycoprotein. On PAGE, unlabeled MSA$_1$ (R.F. 0.33) is stained by Coomassie Blue (protein) and PAS (carbohydrate) but not Sudan Black (lipid) stains (Table I). Upon ultracentrifugation in CsCl, $^{125}$I MSA$_1$ gives a single homogeneous peak with a buoyant density of 1.43±0.01 g/cc (mean±sem, duplicate determinations on 3 preparations). This is within the expected range for a glycoprotein with a substantial carbohydrate content. MSA$_1$ (labeled or unlabeled) binds tightly to Con A, eluting at 0.1 M sugar concentration with α-methyl-mannoside gradients. This suggests that the carbohydrate portion of MSA$_1$ has a high density of terminal sugar residues with α-1,4-glucopyranoside linkages. Most glycoproteins carry a negative charge; purified $^{125}$I MSA$_1$ has an isoelectric point between 3.5–4.5, indicative of such a negative charge. Consistent with a negative charge, MSA$_1$ (labeled and unlabeled) binds easily to the positively charged diethylaminoethyl groups on DEAE.

MSA$_3$ is a homogeneous, relatively easy-to-purify protein. By staining it appears to contain little detectable carbohydrate. Consistent with this is MSA$_3$'s behavior on Concanavalin A Sepharose. Gel filtration and PAGE estimates of its molecular weight are in good agreement.

MSA$_2$ is a heterogeneous lipo-glycoprotein, possibly derived from the miracidial cell membrane. One predominant species is almost invariably isolated from SEA, R.F. 0.22. This species has moderate stability and can be purified to homogeneity as assessed by both SDS and Ornstein-Davis PAGE. Two other species are occasionally observed, one of R.F. 0.08 that is relatively stable but found only in small concentrations, and another (0.18) that appears to be unstable. Very preliminary evidence suggests that some of the antigenic properties of MSA$_2$ are due to MSA$_3$-like activity.

The foregoing characteristics are summarized in Table I.

TABLE I

BIOCHEMICAL PROPERTIES OF PURIFIED MAJOR SEROLOGICAL ANTIGENS

| PAGE[1] | MSA$_1$ | MSA$_3$ | MSA$_2$ Predominant species | MSA$_2$ Occasionally observed species | |
|---|---|---|---|---|---|
| R.F. | 0.34±.01 | 0.48±.01 | 0.22±.01 | 0.08 | 0.18 |
| Staining | | | | | |
| Protein (Coomassie Blue) | + | + | + | + | + |
| Carbohydrate (PAS) = periodic acid Schiff reagent | + | − | + | + | + |
| Lipid (Sudan Black) Schiff reagent | − | − | + | + | + |
| Concanavalin A Binding | Tightly adsorbed | Loosely adsorbed or not adsorbed at all | Loosely adsorbed | | |
| CsCl Buoyant Density | 1.43±.01 g/cc (homogeneous) | 1.54 g/cc[2] | Heterogeneous | N.D. | N.D. |
| MOLECULAR WEIGHT | | | | | |
| Gel Filtration[3] | 138,000±5,000 | 80,000±5,000 | 450,000±8,000 | N.D. | N.D. |
| Velocity Sedimentation[4] | 90–100,000 | 40,000 | >200,000 | N.D. | N.D. |
| PAGE[5] (R.F.) | 50,000 (.50) | 69,000 (.33) | >200,000 | N.D. | N.D.[6] |

TABLE I-continued
BIOCHEMICAL PROPERTIES OF PURIFIED MAJOR SEROLOGICAL ANTIGENS

| PAGE[1] | MSA$_1$ | MSA$_3$ | MSA$_2$ Predominant species | Occasionally observed species |
|---|---|---|---|---|
| Charge (Isoelectric Point) | —(pH 3.5–4.5)[7] | | | |

[1]Discontinuous Polyacrylamide Gel Electrophoresis using 7.5% gel and the method of Ornstein and Davis pH 9.5.
[2]This value may be anomalous due to complexing of MSA$_3$ with Cs$^+$ ions, the properties of this antigen appear to be altered by exposure to this salt.
[3]Sephadex$^R$ G-200 was employed for MSA$_1$, G-100 and G-200 for MSA$_3$, and Biogel®A 1.5 was employed for MSA$_2$ predominant species.
[4]Ultracentrifugation in sucrose gradient; 5–20% for MSA$_1$ and MSA$_2$, 5–20% and 20–40% for MSA$_3$.
[5]10% polyacrylamide gels containing SDS, run after boiling for 15 minutes in SDS and 2ME.
[6]Appears to break down to peptides.
[7]It must be remembered that this value is obtained with purified $^{125}$I-labeled material and that isolation and radiolabeling procedures can alter the charge of a molecule.
[8]Protein adsorbent of known chemical structure.

As stated hereinabove, $^{125}$I MSA$_1$ is both stage and species specific. Antigen competition studies reveal that MSA$_1$ is completely stage specific, as its binding to *S. mansoni* chronic infection serum (CIS) cannot be inhibited either with cercarieal or adult worm antigen. MSA$_2$ and MSA$_3$ are specific with regard to adult worm antigen but their binding to CIS is slightly inhibited by cercarial antigen. Immature eggs in comparison with mature eggs contain only negligible amounts of MSA$_1$ while MSA$_2$ and MSA$_3$ are present in large quantities. Fluid from eggs hatched in spring water (Hatch Fluid - HF) contain considerable amounts of MSA$_1$ as well as MSA$_2$ and MSA$_3$. With regard to species specificity, MSA$_1$ essentially does not cross react with crude soluble egg antigens (SEA) from *S. japonicum* and *S. haematobium* while MSA$_2$ and MSA$_3$ show partial cross reactivity. Antibody dilution studies with sera from animals and humans infected with heterologous schistosome species (i.e. *S. japonicum* and *S. haematobium*) indirectly confirm the high degree of species specificity of MSA$_1$.

Confirmation of species specificity in humans was demonstrated in the following example:

EXAMPLE 3

Sera were obtained from patients in St. Lucia in the West Indies and Machakos, Kenya. The patients on the island of St. Lucia tend to be lightly infected with schistosomiasis and have previously been studied immunologically, parasitologically, and pathologically. Control sera were obtained from patients on the neighboring island of St. Vincent, 30 miles away, where schistosomiasis has never been observed. These St. Vincentians were, however, uniformly infected with non-schistosomal intestinal helminths. Thus, these sera constitute an appropriate control with which to determine whether the MSA$_1$ radioimmunoassay was specific for schistosomiasis among intestinal helminths. For example, among adolescents on St. Vincent, 71% were infected with at least one of the following: *Ascaris lumbricoides*, *Trichuris trichiuria*, or hookworm. All 227 of the St. Lucia/St. Vincent sera analyzed in this example were previously assayed in an earlier study by the Center for Disease Control, Atlanta, Georgia using four commonly used serological tests for schistosomiasis.

The second major population examined, from Kenya, exhibited a low incidence of intestinal helminth infections (Ascaris 1.4%, Trichuris 0.2%, and hookworm 8.9%), and infections with *S. haematobium* are rare (5%).

Finally, two other schistosome-infected populations were studied for the presence of cross-reactive antibodies. Twenty sera samples were obtained from patients in the Philippines infected with *S. japonicum*. From these twenty sera, 15 from patients without pathology (other than hepatosplenomegaly) were selected that roughly age matched 15 adult St. Lucia and 15 adult St. Vincentian patients. Sera were also obtained from children in Kenya that were infected with *S. haematobium*.

The 5 microliter serological test of Example 1 (f) was then carried out with serum from 49 infected adult St. Lucian and 20 uninfected adult St. Vincentian subjects to determine if a binding of more than 50% MSA$_1$ was, in fact, a sensitive assay for schistosome infections. All but one (98%) of the sera from schistosome infected St. Lucians were positive and bound significant amounts of $^{125}$I MSA$_1$. This demonstrates the excellent sensitivity of the MSA$_1$ radioimmunoassay. Sera from the St. Vincentian patients bound no more MSA$_1$ than did the 50 microliters of normal rabbit serum present in the buffer (St. Vincent sera—antigen binding of 20 sera 36.16±S.D.; normal rabbit serum containing buffer—32% antigen binding). There is not significant overlap between the infected (St. Lucia) and the uninfected (St. Vincent) groups. Since intestinal parasites such as the helminths *Trichuris*, *Ascaris*, and hookworm are endemic on St. Vincent, the MSA$_1$ radioimmunoassay apparently is not affected by other helminth infections.

Next, the MSA$_1$ radioimmunoassay was evaluated to determine whether it was capable of differentiating populations infected with the three major species of schistosomes (*S. mansoni, japonicum,* and *haematobium*). Serum obtained from Filipino patients infected with *S. japonicum* contained significant quantities of antibody to *S. mansoni* MSA$_1$ (18/20 parasite positive patients were also positive in the 5 microliter serum, MSA$_1$ radioimmunoassay). Therefore, 0.5 microliters was assayed to quantitate levels of anti-*S. manonsi* MSA$_1$ antibody.

Fifteen sera were selected from adult (mean age=38.4 years old) patients infected with *S. japonicum* but free of serious pathology (ascites, esophageal varices or cerebral manifestations) and therefore assumed to be lightly infected. Sera were also obtained from 15 adult patients with light *S. mansoni* infections on St. Lucia and 15 adult St. Vincentians free of schistosomal infection. Control sera (St. Vincent) did not specifically bind significant amounts of $^{125}$I MSA$_1$ (mean binding 33% versus baseline 32% binding in buffer alone). Sera from *S. japonicum* infected Filipinos specifically bound small (38%) but significant amounts of antigen (p less than 0.001 versus St. Vincent control). Five tenths of a microliter of serum from lightly infected St. Lucians (*S. mansoni*) bound far more antigen (mean 58%). Seven of these sera, even at 0.5 microliters, bound all of the available MSA$_1$ antigen, while the rest of the sera displayed significant but scattered antigen-binding capacities as expected in a quantitative assay. There was some overlap between the anti-*S. mansoni* MSA$_1$ levels of *S. japonicum* and *S. mansoni* infected patients but there was a highly significant difference (p less than 0.001) between the two populations. Thus, the 0.5 microliter quantitative MSA$_1$ radioimmunoassay can distinguish these two schistosome infected populations.

Finally an attempt was made with the 0.5 microliter serum, MSA$_1$ radioimmunoassay to differentiate populations infected with *S. mansoni* and *S. haematobium*. These two schistosome species appear to be closely related and even the most sophisticated serologic tests have difficulties differentiating *S. haematobium* infections from those with *S. mansoni*. A group of adolescent and pediatric patients was selected, moderately heavily infected with *S. haematobium*. These were age matched to a group of patients with moderately heavy *S. mansoni* infections. 93% of the *S. haematobium* patients were positive in the 5 microliter serum, MSA$_1$ radioimmunoassay. However, when their sera were assayed in the 0.5 microliter quantitative assay there was almost no overlap in the frequency distribution of their antigen-binding values compared to those of the *S. mansoni* population. Thus, patients infected with *S. haematobium*, although they produce antibody that reacts with *S. mansoni* MSA$_1$, produce far less of it than do patients with comparable *S. mansoni* infections.

Table II compares the results of the radioimmunoassay (RIA) on the St. Lucia/St. Vincent patients employing MSA$_1$ with the results of four other tests conducted by the Center for Disease Control, referred to hereinabove. The other tests are far more expensive, require far more material and are not as reliable.

TABLE II

| TEST | PEDIATRIC | | ADOLESCENT | | ADULT | | Net Score % Diagnosed % False+ |
|---|---|---|---|---|---|---|---|
| | St. Lucia | St. Vincent | St. Lucia | St. Vincent | St. Lucia | St. Vincent | |
| Complement fixation | 33% | 9% | 58% | 6% | 62% | 33% | 54%/12% |
| Cholesterol Lecithin Flocculation | 19% | 6% | 57% | 8% | 47% | 0% | 48%/6% |
| Sensitive immunofluoroescence (.1%BS .1% BSA) | 61% | 6% | 76% | 12% | 82% | 0% | 74%/8% |
| Specific immunofluoroescence (1% BSA) | 44% | 0% | 72% | 2% | 76% | 0% | 67%/1% |
| MSA$_1$ RIA | 64% | 0% | 83% | 0% | 98% | 0% | 81%/0% |
| Number of Patients | 36 | 32 | 50 | 40 | 49 | 20 | 227 |

It will be appreciated that the instant specification and examples are set forth by way of illustration and not limitation, and that various modifications and changes may be made without departing from the spirit and scope of the present invention.

What is claimed is:

1. A fraction of *Schistosoma mansoni* egg antigen specific to *Schistosoma mansoni* mature eggs, and which has the following properties:

| | |
|---|---|
| Polyacrylamide gel R.F. Staining | 0.34 ± 0.01 |
| Protein (Coomassie Blue) | + |
| Carbohydrate (Periodic acid, Schiff reagent) | + |
| Lipid (Sudan Black) | — |
| Concanavalin A Binding | Tightly Adsorbed |
| CsCl Buoyant Density | 1.43 ± .01 g/cc |
| MOLECULAR WEIGHT | (homogeneous) |
| Gel Fitration | 148,000 ± 5,000 |
| Velocity Sedimentation | 90–100,000 |
| Polyacrylamide gel (R.F.) | 50,000 (.50) |
| Charge (Isoelectric Point) | pH 3.514 4.5 | said fraction being suitable to detect Schistosomiasis.

2. A fraction according to claim 1, which is radioactively labeled.

3. A fraction according to claim 1, which is radioactively labeled with $^{125}$I.

4. A fraction of *Schistosoma mansoni* egg antigen which has the following approximate properties:

| | |
|---|---|
| Polyacrylamide gel R.F. Staining | 0.48 ± 0.01 |
| Protein (Coomassie Blue) | + |
| Carbohydrate (Periodic acid, Schiff reagent) | — |
| Lipid (Sudan Black) | — |
| Concanavalin A Binding | Loosely adsorbed or not adsorbed at all |
| CsCl Buoyant Density | 1.53 g/cc$^2$ |
| MOLECULAR WEIGHT | |
| Gel Filtration | 80,000 ± 5,00 |
| Velocity Sedimentation | 40,000 |
| Polyacrylamide gel (R.F.) | 69,000 (.33) | said fraction being suitable to detect Schistosomiasis.

5. A fraction of *Schistosoma mansoni* egg antigen which has the following approximate properties:

| | Predominant species | Occasionally observed species | |
|---|---|---|---|
| Polyacrylamide gel R.F. Staining | 0.22 ± .01 | 0.08 | 0.18 |
| Protein (Coomassie Blue) | + | + | + |
| Carbohydrate (Periodic acid, Schiff reagent) | + | + | + |
| Lipid | + | + | + |
| Concanavalin A Binding | Loosely adsorbed | | |
| CsCl Buoyant Density | Heterogeneous (1.51–1.37) | N.D. | N.D. |
| MOLECULAR WEIGHT | | | |
| Gel Filtration | 450,000±8,000 | N.D. | N.D. |
| Velocity Sedimentation | 200,000 | N.D. | N.D. |
| Polyacrylamide gel (R.F.) | 200,000 | N.D. | N.D. | said fraction being suitable to detect Schistosomiasis.

6. The process for fractionating *Schistosoma mansoni* egg antigen comprising grinding *Schistosoma mansoni* eggs in water to form a solution thereof, subjecting said solution to affinity chromatography and eluting to form a third fraction which was most lightly held, a second fraction which was less lightly held and a first fraction which was strongly held, and purifying at least said first fraction, said first fraction containing antigens as defined in claim 1 specific to *Schistosoma mansoni* mature eggs.

7. The process of claim 6, wherein said affinity chromatography is effected on a galactan, elution of said first fraction is effected by at least one of $\alpha$-methyl mannoside or $\alpha$-methyl glucoside, and including the further step of radioactively labeling said first fraction.

8. The process of claim 7, wherein the radioactive labeling is effected with $^{125}I$.

9. The process of claim 6, wherein purification of at least the first fraction is effected by ion exchange chromatography using a salt eluant, any third fraction material present being most lightly held, any second fraction material present being less lightly held, and the first fraction material being most strongly held.

10. The process of claim 8, wherein purification of at least the first fraction is effected by ion exchange chromatography using a salt eluant, any third fraction material present being most lightly held, any second fraction material being less lightly held, and the first fraction material being most strongly held, and further including desalting said first fraction at some stage subsequent to radioactive labeling to remove at least part of any salts introduced during said radioactive labeling.

11. A process for determining the presence of antibodies to mature schistosome eggs in a patient's serum comprising mixing said serum with a radioactively labeled fraction produced by the process of claim 7, separating any precipitate which forms, and measuring the radioactivity of said precipitate, the level of radioactivity being an index of the amount of antibodies to mature schistosome eggs in said serum.

12. A process for determining the presence of antibodies to mature *Schistosoma mansoni* eggs in a patient's serum comprising mixing said serum with a radioactively labeled fraction according to claim 2, separating any precipitate which forms, and measuring the radioactivity of said precipitate, the level of radioactivity being an index of the amount of antibodies to *Schistosoma mansoni* eggs in said serum.

* * * * *

UNITED STATES PATENT AND TRADEMARK OFFICE
CERTIFICATE OF CORRECTION

PATENT NO. : 4,158,049
DATED : June 12, 1979
INVENTOR(S) : Ronald Peter Pelley et al It is certified that error appears in the above-identified patent and that said Letters Patent are hereby corrected as shown below:

TABLE I, column 5, line 7, delete "PAGE$^1$", and insert --PAGE $^1$-- between lines 8 and 9.

Claim 5, line 34, delete "Predominant" and "Occasionally", and insert --Predominant-- between lines 45 and 46 over the word "species";

insert --Occasionally-- between lines 45 and 46 over the words "observed species".

Claim 5, delete "Polyacrylamide gel R.F." on line 46, and insert --Polyacrylamide gel R.F.-- between lines 47 and 48.

*Signed and Sealed this*

*Twenty-ninth* Day of *April 1980*

[SEAL]

Attest:

SIDNEY A. DIAMOND

*Attesting Officer*  *Commissioner of Patents and Trademarks*